(12) United States Patent
Le Nestour et al.

(10) Patent No.: US 7,968,532 B2
(45) Date of Patent: Jun. 28, 2011

(54) TREATMENT OF GYNECOMASTIA WITH 4-HYDROXY TAMOXIFEN

(75) Inventors: Elisabeth Le Nestour, Paris (FR); Andrew Palumbo, Brooklyn, NY (US)

(73) Assignee: Besins Healthcare Luxembourg, Luxembourg (LU)

(*) Notice: Subject to any disclaimer, the term of this patent is extended or adjusted under 35 U.S.C. 154(b) by 814 days.

(21) Appl. No.: 11/009,390

(22) Filed: Dec. 13, 2004

(65) Prior Publication Data
US 2005/0158388 A1 Jul. 21, 2005

Related U.S. Application Data

(60) Provisional application No. 60/529,415, filed on Dec. 15, 2003.

(30) Foreign Application Priority Data

Dec. 15, 2003 (EP) ..................... 03293156

(51) Int. Cl.
 *A61K 31/33* (2006.01)
 *A01N 43/00* (2006.01)
(52) U.S. Cl. ....................................... 514/183
(58) Field of Classification Search ............... None
See application file for complete search history.

(56) References Cited

U.S. PATENT DOCUMENTS

| | | | |
|---|---|---|---|
| 4,919,937 A | 4/1990 | Mauvais-Jarvis et al. | |
| 4,973,755 A | 11/1990 | Grafe et al. | |
| 5,045,553 A * | 9/1991 | Ueda et al. .............. | 514/344 |
| 5,613,958 A | 3/1997 | Kochinke et al. | |
| 5,720,963 A | 2/1998 | Smith | |
| 5,820,877 A | 10/1998 | Yamaguchi et al. | |
| 5,904,930 A | 5/1999 | Fischer et al. | |
| 5,945,109 A | 8/1999 | Schmidt et al. | |
| 6,013,270 A | 1/2000 | Hargraves et al. | |
| 6,503,894 B1 | 1/2003 | Dudley et al. | |
| 6,632,841 B1 | 10/2003 | Af Ursin et al. | |
| 7,485,623 B2 * | 2/2009 | Bua ......................... | 514/12 |
| 7,507,769 B2 | 3/2009 | Nestour | |
| 7,704,516 B2 | 4/2010 | Drouin et al. | |
| 7,767,147 B2 | 8/2010 | Adachi et al. | |
| 7,786,172 B2 | 8/2010 | De Lignieres | |
| 2001/0041718 A1 * | 11/2001 | Thompson et al. ........ | 514/317 |
| 2002/0115676 A1 | 8/2002 | MacLean | |
| 2003/0065017 A1 | 4/2003 | HuaZhu et al. | |
| 2003/0087885 A1 | 5/2003 | Masini-Eteve et al. | |
| 2003/0150876 A1 | 8/2003 | Walters et al. | |
| 2003/0175329 A1 | 9/2003 | Azarnoff et al. | |
| 2004/0009994 A1 * | 1/2004 | MacLean et al. ......... | 514/266.2 |
| 2004/0086552 A1 | 5/2004 | Klokkers et al. | |
| 2004/0138314 A1 | 7/2004 | Bua | |
| 2005/0031695 A1 | 2/2005 | Rouanet et al. | |
| 2005/0032909 A1 | 2/2005 | Lignieres et al. | |
| 2005/0208139 A1 | 9/2005 | Hilt et al. | |
| 2005/0209340 A1 | 9/2005 | Le Nestour | |
| 2006/0105041 A1 | 5/2006 | Masini-Eteve | |
| 2009/0186944 A1 | 7/2009 | Rouanet et al. | |

FOREIGN PATENT DOCUMENTS

| | | |
|---|---|---|
| DE | 32 38 984 | 5/1983 |
| DE | 38 36 862 A1 | 5/1990 |
| EP | 0 513 832 | 11/1992 |
| EP | 0 792 640 A2 | 9/1997 |
| EP | 1 579 856 A1 | 9/2005 |
| EP | 1 579 857 A1 | 9/2005 |
| WO | WO-95/24187 | 9/1995 |
| WO | WO 97/36570 A1 | 10/1997 |
| WO | WO 99/33451 | 7/1999 |
| WO | WO 01/43775 | 6/2001 |
| WO | WO 2004/110420 | 12/2004 |
| WO | WO-2004/110420 A | 12/2004 |

OTHER PUBLICATIONS www.wrongdiagnosis,com/g/gynecomastia/book-diseases-3a.htm. 2000. 5 sheets.*
Rohrich et al. Classification and management of gynecomastia: defining the role of ultrasound-assited liposuction. Plastic and Reconstruction Surgery, Feb. 2003, vol. 111, Issue 2, pp. 909-923.*
Hashimoto et al. Breast Imaging—A Correlative Atlas. Thieme Medical Publishers, Inc., 2003. pp. 360-361.*
J.D. Gagnon et al., "Pre-Estrogen Breast Irradiation for Patients with Carcinomia of the Prostate: a critical review", Journal of Urology, vol. 121:182-184, (1979).
N. Giambiagi et al., "Immunological Differences Between the Estradiol-, Tamxifen- and 4-Hydroxy-Tamoxifen-Estrogen Receptor Complexes Detected by Two Monoclonal Antibodies", J. Steroid Biochem. vol. 30, No. 1-6, pp. 213-217, 1988.
A.R. Glass, "Gynecomastia", Endocrinology and Metabolism Clinics of North America: Clinical Andrology, vol. 23, No. 4, pp. 825-837 (1994).
U. Gruntmanis et al., "Treatment of Gynecomastia", Current Opinion in Investigational Drugs, vol. 2, No. 5, pp. 643-649 (2001). V. Craig Jordan et al., "Metabolites of tamoxifen in animals and man: identification, pharmacology, and significance", Breast Cancer Research and Treatment, 2, pp. 123-138.
George G.J.M. Kuiper et al., "Comparison of the Ligand Binding Specificity and Transcript Tissue Distribution of Estrogen Receptors α and β", Endocrinology, vol. 138, No. 3, 1997, pp. 863-870.
Frédérique Kuttenn et al., "Médecine et Thérapeutique", C.R. Acad. Sc. Paris Série III, No. 12, 1985, 300:457-462.
Carmen Lazala et al., "Pubertal Gynecomastia", Journal of Pediatric Endocrinology & Metabolism, 15:553-560 (2002).
Catherine Malet et al., "Tamoxifen and Hydroxytamoxifen Isomers *versus* Estradiol Effects on Normal Human Breast Cells in Culture", Cancer Research, vol. 48, No. 24, Dec. 15, 1988, pp. 7193-7199.
Ruchi Mathur et al., "Gynecomastia: Pathomechanisms and treatment strategies", Horm. Res., 48:95-102 (1997).

(Continued)

*Primary Examiner* — Brandon J Fetterolf
*Assistant Examiner* — Anna Pagonakis
(74) *Attorney, Agent, or Firm* — Foley & Lardner LLP

(57) ABSTRACT

The present invention provides methods for treating and preventing gynecomastia by administering 4-hydroxy tamoxifen to a patient. When percutaneously administered to a patient's breasts, 4-hydroxy tamoxifen concentrates locally, and exerts an anti-estrogenic effect. In patients with gynecomastia, this reduces the effective estrogen-androgen ratio in the breast tissue, thereby reducing ductal proliferation, epithelial and stromal hyperplasia, and pain. In patients at risk for developing gynecomastia, 4-hydroxy tamoxifen's anti-estrogenic effect prevents tissue proliferation and its accompanying pain.

20 Claims, 2 Drawing Sheets

OTHER PUBLICATIONS

Pierre Mauvais-Jarvis et al., "trans-4-Hydroxytamoxifen Concentration and Metabolism after Local Percutaneous Adminstration to Human Breast", Cancer Research, vol. 46, Mar. 1986, pp. 1521-1525.

Henri Pujol et al., "Phase 1 study of percutaneous 4-hydroxy-tamoxifen with analysis of 4-hydroxy-tamoxifen concentrations in breast cancer and normal breast tissue", Cancer Chemother. Pharmacol., 36:493-498 (1995).

Lawrence H. Block Ph.D., Epidermal and Transdermal Drug Delivery, Medicated Topicals, Chapter 44, pp. 836-857.

David W. Robertson et al., "Synthesis of the E and Z Isomers of the Antiestrogen Tamoxifen and Its Metabolite, Hydroxytamoxifen, in Tritium-Labeled Form", J. Org. Chem., 1982, vol. 47, No. 12, pp. 2387-2393.

David W. Robertson et al., "Tamoxifen Antiestrogens, A Comparison of the Activity, Pharmacokinetics, and Metabolic Activation of the CIS and Trans Isomers of Tamoxifen" Journal of Steroid Biochemistry, vol. 16, pp. 1-13, (1982).

Hironobu Sasano et al., "Aromatase and Steroid Receptors in Gynecomastia and Male Breast Carcinoma: An Immunohistochemical Study", Journal of Clinical Endocrinoly and Metabolisms, vol. 81, No. 8, pp. 3063-3067 (1996).

Fabrice Sauvez et al., "Cutaneously applied 4-hydroxytamoxifen is not carcinogenic in female rats", Carcinogenesis vol. 20, No. 5, pp. 843-850 1999.

B.S. Shoker et al., "Abnormal Regulation of the Oestrogen Receptor in Benign Breast Lesions", J. Clin. Pathol., 53:778-783 (2000).

Ashini L. Wijayaratne et al., "Comparative Analyses of Mechanistic Differences Among Antiestrogens", Endocrinology, vol. 140, No. 2, pp. 5828-5840.

Brisson, et al., "Tamoxifen and Mammographic Breast Densities", Cancer Epidemiology, Biomarkers & Prevention, vol. 9, 911-915 (2000).

"High Breast Density a Risk Factor", pp. 1-4, http://www.breastcancer.org/research_genetics_091902_pf.html (Aug. 11, 2005).

Lawrence N. Parker et al., "Treatment of Gynecomastia with Tamoxifen: A Double Blind Crossover Study", Metabolism, vol. 35, No. 8 Aug. 1986, pp. 705-708.

Alberti et al.; "In Vivo Assesment of Enhanced Topical Delivery of Terbinafine to Human Stratum Corneum"; J. of Controlled Release; 71:319-327 (2001).

Bodian, Ph.D. et al.; "Prognostic Significance of Benign Proliferative Breast Disease;" Cancer, Jun. 15, 1993; vol. 71, No. 12, pp. 3896-3907.

Tan-Chiu, et al.; "Effects of Tamoxifen on Benign Breast Disease in Women at High Risk for Breast Cancer;" Journal of the National Cancer Institute; vol. 95, No. 4, Feb. 19, 2003, pp. 302-307.

Fentiman, I.S. et al., "Dosage and duration of tamoxifen treatment for mastalgia: a controlled trial," Br. J. Surg. 1988, vol. 75, September, 845-846.

Fentiman, I.S. et al., "Studies of tamoxifen in women with mastalgia," The British Journal of Clinical Practice, Supplement 68, vol. 43, No. 11, Nov. 1989, pp. 34-36.

Fentiman, Ian S., "Tamoxifen and Mastalgia an Emerging Indication," Drugs, vol. 32, No. 6, Dec. 1986, pp. 477-480.

Friend et al; "Simple Alkyl Esters as Skin Permeation Enhancers;" Journal of Controlled Release; 9(1):33-31 (Jun. 1989) (Abstract only).

IBIS Investigators; "First Results from the International Breast Cancer Intervention Study (IBIS-I): a Randomised Prevention Trial;" The Lancet; 360:817-824 (Sep. 14, 2002).

Kutten, F. et al.; "Principe de l'adminstration percutanée des antiestrogénes en pathologie mammaire;" Contracept. Fertil. Sex., 1991, vol. 19, No. 2, pp. 165-171 (with Abstract).

Lee, et al.; Quantification of tamoxifen and three metabolites in plasma by high-performance liquid chromatography with fluorescence detection: application to a clinical trial; Journal of Chromatography B.; 791 (2003), pp. 245-253.

Malet C. et al; "Effect of 4-hydroxytamoxifen isomers on growth and ultrastructural aspects of normal human breast epithelial (HBE) cells in culture"; The Journal of Steroid Biochemistry & Molecular Biology, 2002, vol. 82, pp. 289-296.

Mansel, et al.; "A Double Blind Trial of a Prolactin Inhibitor Bromocriptine in Painful Benign Breast Disease;" Br. J. Surg.; 65:724-727 (1978).

Mauvais-Jarvis, "Mastodynia and Fibrocystic Disease," Current Therapy in Endocrinology and Metabolism, 3:280-284 (1988).

Mauvais-Jarvis, P., "Hormonal Therapy of Benign Breast Disease," Senologie et Pathologie Mammaire. 4ème Congrès International, Paris Sep. 1-4, 1986, pp. 128-132.

Mauvais-Jarvis, P., "Le Traitement Hormonal des Mastopathies Bénignes," Bull Cancer 78:365-371 (1991).

Murphy, C.S. et al., Structure-Function Relationships of Hydroxylated Metabolites of Tamoxifen that Control the Proliferation of Estrogen-Responsive T47D Breast Cancer Cells In Vitro, Molecular Pharmacology 38:737-743 (1990).

Ruland et al., "Influence of Various Penetration Enhancers on the In Vitro Permeation of Amino Acids Across Hairless Mouse Skin," International Journal of Pharmaceutics, 85(1-3):7-17 (Sep. 1992).

Santoyo et al., "Penetration Enhancer Effects on the In Vitro Percutaneous Absorption of Piroxicam Through Rat Skin," International Journal of Pharmaceutics, 117:219-224 (1995).

Simony-Lafontaine, I. et al., "Neoadjuvant Percutaneous-4-Hydroxytamoxifen Decreases Breast Cancer Cell Proliferation: A Prospective Randomized Image Analysis Study," Analytical Cellular Pathology, 25(5-6): 258-259 (Oct. 1, 2003), XP009030125.

Wolfe, John N. MD, "Risk For Breast Cancer Development Determined By Mammographic Parenchymal Pattern," Cancer, May 1976, vol. 37, No. 5, pp. 2486-2492.

Office Action issued Feb. 8, 2008, in U.S. Appl. No. 10/805,528, 9 pages.

Office Action issued Feb. 9, 2007, in U.S. Appl. No. 10/805,528, 8 pages.

Office Action issued Jul. 17, 2006, in U.S. Appl. No. 10/805,528, 11 pages.

Office Action issued Nov. 2, 2005, in U.S. Appl. No. 10/805,528, 9 pages.

Office Action issued Oct. 4, 2007, in U.S. Appl. No. 10/734,644, 11 pages.

Office Action issued Apr. 10, 2007, in U.S. Appl. No. 10/734,644, 10 pages

Office Action issued Feb. 24, 2006, in U.S. Appl. No. 10/734,644, 10 pages.

Office Action issued Aug. 23, 2005, in U.S. Appl. No. 10/734,644, 14 pages.

Notice of Allowance issued Jun. 24, 2008, in U.S. Appl. No. 10/734,644, 6 pages.

Office Action issued Dec. 11, 2007, in U.S. Appl. No. 10/734,638, 20 pages.

Office Action issued Mar. 13, 2007, in U.S. Appl. No. 10/734,638, 20 pages.

Office Action issued Oct. 2, 2006, in U.S. Appl. No. 10/734,638, 15 pages.

Office Action issued May 5, 2006, in U.S. Appl. No. 10/734,638, 22 pages.

Office Action issued Jun. 18, 2008, in U.S. Appl. No. 10/858,399, 14 pages.

Office Action issued Nov. 1, 2008, in U.S. Appl. No. 10/858,399, 20 pages.

Notice of Allowance issued Jun. 13, 2008, by the Examiner in U.S. Appl. No. 10/734,638 (US 2005/0031695).

Office Action issued Jan. 6, 2009, by the Examiner in U.S. Appl. No. 10/734,638 (US 2005/0031695).

Notice of Allowance issued Nov. 7, 2008, by the Examiner in U.S. Appl. No. 10/805,528.

Office Action issued Feb. 5, 2009, by the Examiner in U.S. Appl. No. 10/858,399 (US 2005/0032910).

Office Action issued May 5, 2009, by the Examiner in U.S. Appl. No. 11/249,122 (US 2006/0105041).

Office Action issued Dec. 16, 2008, by the Examiner in U.S. Appl. No. 10/734,640 (US 2005/0032909).

Office Action issued May 29, 2008, by the Examiner in U.S. Appl. No. 10/734,640 (US 2005/0032909).

Office Action issued Aug. 23, 2007, by the Examiner in U.S. Appl. No. 10/734,640 (US 2005/0032909).

Office Action issued Mar. 12, 2007, by the Examiner in U.S. Appl. No. 10/734,640 (US 2005/0032909).
Office Action issued on Aug. 18, 2009, by the Examiner in U.S. Appl. No. 10/858,399 (US 2005/0032910).
Office Action issued on May 19, 2009, by the Examiner in U.S. Appl. No. 10/858,399 (US 2005/0032910).
Office Action issued on Aug. 4, 2009, by the Examiner in U.S. Appl. No. 10/734,640 (US 2005/0032909).
Notice of Allowance issued on Dec. 22, 2009, by the Examiner in U.S. Appl. No. 10/734,638 (US 2005/0031695).
Office Action issued on Nov. 12, 2009, by the Examiner in U.S. Appl. No. 10/734,638 (US 2005/0031695).
Office Action issued on Dec. 3, 2009, by the Examiner in U.S. Appl. No. 11/249,122 (US 2006/0105041).
Office Action issued on Sep. 15, 2009, by the Examiner in U.S. Appl. No. 10/805,530 (US 2005/0208139).
Atkinson, Charlotte et al., "Mammographic Patterns as a Predictive Biomarker of Breast Cancer Risk: Effect of Tamoxifen," *Cancer Epidemiology, Biomarkers & Prevention*, vol. 8, Oct. 1999, pp. 863-866.
Bevitt, Debra J. et al., "New Monoclonal Antibodies to Oestrogen and Progesterone Receptors Effective for Paraffin Section Immunohistochemistry," *Journal of Pathology*, vol. 183, (1997) pp. 228-232.
Boyd, N.F. et al., "Quantitative Classification of Mammographic Densities and Breast Cancer Risk: Results from the Canadian National Breast Screening Study," *Journal of the National Cancer Institute*, vol. 87, No. 9, May 3, 1995, pp. 670-675.
Boyd, N.F. et al., "Relationship Between Mammographic and Histological Risk Factors for Breast Cancer," *Journal of the National Cancer Institute*, vol. 84, No. 15, Aug. 5, 1992, pp. 1170-1179. (mammography).
Boyd, Norman F. et al., "Effects at Two Years of a Low-Fat High-Carbohydrate Diet on Radiologic Features of the Breast: Results from a Randomized Trial," *Journal of the National Cancer Institute*, vol. 89, No. 7, Apr. 2, 1997, pp. 488-496.
Byrne, Celia, "Studing Mammographic Density: Implications for Understanding Breast Cancer," *Journal of the National Cancer Institute*, vol. 89, No. 8, Apr. 16, 1997, pp. 531-537.
Charlier, Corinne et al., "Tamoxifen and Its Active Metabolite Inhibit Growth of Estrogen Receptor-Negative MDA-MB-435 Cells," *Biochemical Pharmacology*, vol. 49, No. 3, pp. 351-358, 1995.
Fajardo et al., "Correlation Between Breast Parenchymal Patterns and Mammogrpahers' Certainty of Diagnosis," *Investigative Radiology*, vol. 23, Jul. 1988, pp. 505-508.
Gerdes et al, "Cell Cycle Analysis of a Cell Proliferation-Associated Human Nuclear Antigen Defined By The Monoclonal Antibody Ki-671," *The Journal of Immunology*, 133(4):1710-1715, 1984.
Girault, J. et al., "Quantitative Measurement of 4-Hydroxy Tamoxifen in Human Plasma and Mammary Tumours by Combined Gas Chromatography/Negative Chemical Ionization Mass Spectrometry," *Biological Mass Spectrometry*, vol. 22, (1993) pp. 395-402.
Gura, Trisha, "Cancer Models: Systems for Identifying New Drugs Are Often Faulty," *Science*, vol. 278, Nov. 7, 1997, pp. 1041-1042.
Harvey, Jennifer A. et al., "Short-term Cessation of Hormone Replacement Therapy and Improvement of Mammographic Specificity," *Journal of the National Cancer Institute*, vol. 89, No. 21, Nov. 5, 1997, pp. 1623-1625.
Harvey, Susan C. et al., "Marked Regression of a Nonpalpable Breast Cancer After Cessation of Hormone Replacement Therapy," *American Journal of Roentgenology*, Aug. 1996, 167:394-395.
Jenks, Susan, "Dense Breast Tissues May Hold Increased Cancer Risk for Some," *Journal of the National Cancer Institute*, vol. 86, No. 8, Apr. 20, 1994, pp. 578-580 (1982).
Kaufman, Z. et al., "The Mammographic Parenchymal Patterns of Women on Hormonal Replacement Therapy," *Clinical Radiology* (1991), 43, 389-392.
Kerlikowske, Karla MD et al., "Effect of Age, Breast Density, and Family History on the Sensitivity of First Screening Mammography," *JAMA*, vol. 276, No. 1, Jul. 3, 1996, pp. 33-38.
Kolb, Thomas M. MD et al., "Comparison of the Performance of Screening Mammography, Physical Examination, and Breast US and Evaluation of Factors that Influence Them: An Analysis of 27,825 Patient Evaluations," *Radiology*, vol. 225, No. 1, Oct. 2002, pp. 165-175 (mammography).
Korenman, Stanley G. et al., "Estradiol Radioimmunoassay Without Chromatography: Procedure, Validation And Normal Values," *J. Clin. Endocrinol. Metab.* 38:718-720 (1974).
Leung, Winnie MD et al., "Mammographic density in women on postmenopausal hormone replacement therapy," *SURGERY*, vol. 122, No. 4, Oct. 1997, pp. 669-674.
Ma, L. et al., "Case-Control Study of Factors Associated With Failure to Detect Breast Cancer by Mammography," *Journal of the National Cancer Institute*, vol. 84, No. 10, May 20, 1992, pp. 781-784.
Nemani, Mona et al., "Activation of the human homologue of the *Drosophila sina* gene in apoptosis and tumor suppression," *Proc. Natl. Acad. Sci. USA*, vol. 93, pp. 9039-9042, Aug. 1996.
Nomura, Y. et al., "Effects of antiestrogens and medroxyprogesterone acetate on the clonogenic growth of tamoxifen-sensitive and resistant human breast cancer cells," *Jpn. J. Cancer Chemotherapy*, 12(4): 844-850 (1985).
Rutter, Carolyn M. PhD et al., "Changes in Breast Density Associated With Initiation, Discontinuation. and Continuing Use of Hormone Replacement Therapy," *JAMA*, vol. 285, No. 2, Jan. 10, 2001, pp. 171-176.
Saftlas, Audrey F. et al., "Mammographic Parenchymal Patterns And Breast Cancer Risk," *Epidemiologic Reviews*, vol. 9, 1987, pp. 146-174.
Schlüter, Carsten et al. "The Cell Proliferation-associated Antigen of Antibody Ki-67: A Very Large, Ubiquitous Nuclear Protein with Numerous Repeated Elements, Representing a New Kind of Cell Cycle-maintaining Proteins," *The Journal of Cell Biology*, vol. 123, 1993, pp. 513-522.
Son, Hong Ju et al., "Significance of Follow-Up Mammography in Estimating the Effect of Tamoxifen in Breast Cancer Patients Who Have Undergone Surgery," *American Journal of Roentgenology*, 173: 905-909 (Oct. 1999).
Spicer, Darcy V. et al., "Changes in Mammographic Densities Induced by a Hormonal Contraceptive Designed to Reduce Breast Cancer Risk," *Journal of the National Cancer Institute*, vol. 86, No. 6, Mar. 16, 1994, pp. 431-436.
Tan et al., "Effect of Carbopol and Polyvinylpyrrolidone on the Mechanical, Rheological, and Rlease Properties of Bioadhesive Polyethylene Glycol Gels," *AAPS PharmSciTech*, 2000, 1(3), Article 24 (http://www.pharmscitech.com).
Ursin, Giske et al., The Detection of Changes in Mammographic Densities, *Cancer Epidemiology, Biomarkers & Prevention*, vol. 7, Jan. 1998, pp. 43-47.
Waseem, Naushin H. et al., "Monoclonal Antibody Analysis of the Proliferating Cell Nuclear Antigen (PCNA) Structural conservation and the detection of a nucleolar form," *Journal of Cell Science*, 96, 121-129 (1990).
Office Action issued on Jan. 16, 2007 by the Examiner in U.S. Appl. No. 10/734,638 (US 7,704,516).
Office Action issued on Jul. 7, 2006 by the Examiner in U.S. Appl. No. 10/734,644 (US 7,485,623).
Office Action issued on Feb. 2, 2010 by the Examiner in U.S. Appl. No. 10/805,530 (US 2005/0208139).
Notice of Allowance issued on Feb. 2, 2010 by the Examiner in U.S. Appl. No. 10/734,640 (US 2005/0032909).
Notice of Allowance issued on Jan. 20, 2010 by the Examiner in U.S. Appl. No. 10/858,399 (US 2005/0032910).
Hashimoto et al., "Section VI—Increased Density," "Section VIII—Male Breast," *Breast Imaging—A Correlative Atlas*, Thieme Meical Publishers, Inc., 2003.
Qazi et al., "Diagnosis and Management of Male Breast Enlargement in Patients with HIV/AIDS," *AIDS Read.*, 10(12), 2000, http://www.medscape.com/viewarticle/41036.
Petroudi et al., "Automatic Classification of Mammographic Parenchymal Patterns: A Statisitical Approach," *FEEE Conf. Eng. Med. Biol. Soc.*, 1:798-801, 2003.
Rohrich et al., "Classification and Management of Gynecomastia: Defining the Role of Ultrasound-Assisted Liposuction," *Plastic and Reconstruction Surgery*, 111(2): 909-923. Feb. 2003.

Hashimoto et al., "Section VIII: Male Breast," *Breast Imaging: A Correlative Atlas*, Thieme Medical Publishers, pp. 359 and 366-369, 2003.

Office Action issued on Aug. 25, 2010 by the Examiner in U.S. Appl. No. 12/353,890 (US 2009/0186944).

Office Action issued on Apr. 9, 2010 by the Examiner in U.S. Appl. No. 11/249,122 (US 2006/0105041).

Office Action issued on Nov. 4, 2010 by the Examiner in U.S. Appl. No. 10/805,530 (US 2005/0208139).

Fournier et al., "Hormonal and Non-Hormonal Medical Therapy of Benign Breast Disease," *Horm. Res.*, vol. 32 (suppl.), pp. 28-31, 1989.

J. Barrat et al., "Effet in vivo de l'administration locale de progestérone sur l'activité mitotique des galactophores humains", J. Gynecol. Obstet. Biol. Reprod. 19: 269-274 1990.

G.D. Braunstein, "Aromatase & Gynecomastia", Endocr. Relat. Cancer, 6:315-324 (1999).

Bronaugh & Maibach, "Percutaneous Absorption Drugs-Cosmetics-Mechanisms-Methodology", Marcel Dekker Inc., New York, 1999.

Philip Carthew et al., "Cumulative exposure to tamoxifen: DNA adducts and liver cancer in the rat", Arch Toxicol (2001) 75: 375-380.

Gerard Chetrite et al., "Effect of Promegestone, Tamoxifen, 4-Hydroxytamoxifen and ICI 164,384 on the Oestrone Sulphatase Activity of Human Breast Cancer Cells", Anticancer Research 13: 931-934 (1993).

I.R. Daniels et al., "Gynecomastia", Eur. J. Surg. 167:885-892 (2001).

Eric C. Dietze et al., "Tamoxifen but Not 4-Hydroxytamoxifen Initiates Apoptosis in p53(-) Normal Human Mammary Epithelial Cells by Inducing Mitochondrial Depolarization", The Journal of Biological Chemistry vol. 276, No. 7, Issue of Feb. 16, 2001, pp. 5384-5394.

* cited by examiner

FIGURE 1: Representation of Tamoxifen Metabolism
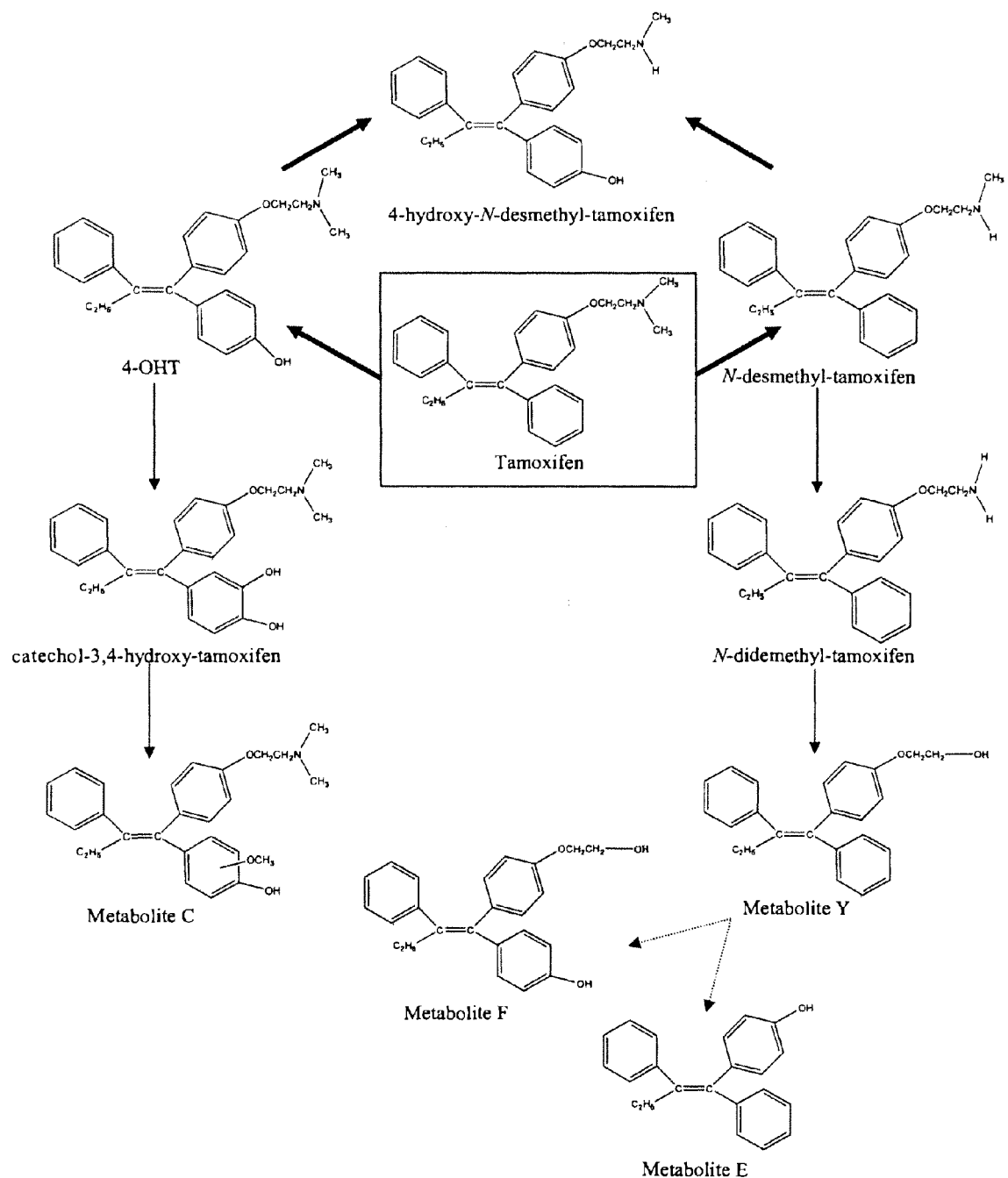

Figure 2: Mean ± SD Plasma Concentration of 4-hydroxy tamoxifen in Healthy Women Following Last Cutaneous Administration (Day 25 of the Second Cycle)
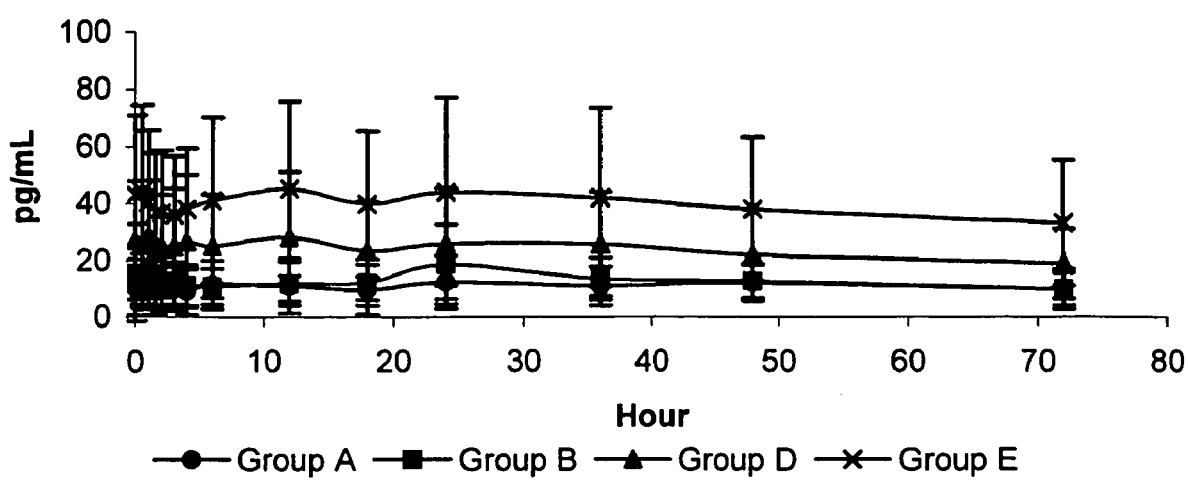

TREATMENT OF GYNECOMASTIA WITH 4-HYDROXY TAMOXIFEN

CROSS-REFERENCE TO RELATED APPLICATIONS

This application claims benefit of priority to U.S. application No. 60/529,415, filed Dec. 15, 2003, and European application No. 03 293 156, filed Dec. 15, 2003, both of which are incorporated herein by reference.

BACKGROUND OF THE INVENTION

The present invention relates to the prevention and treatment of gynecomastia with 4-hydroxy tamoxifen (4-OHT).

Gynecomastia is a common clinical condition, often presenting secondarily to an underlying disorder, representing the benign and sometimes painful proliferation of breast tissue in young boys and adult males (Mathur and Braunstein, 1997). During the early, or florid phase, of the condition, breast tissue undergoes ductal proliferation accompanied by epithelial and stromal hyperplasia. After prolonged periods of time, the florid phase gives way to a fibrotic phase characterized by increased stromal hyalinization and dilation of the ducts. In many individuals, gynecomastia spontaneously regresses.

Generally, gynecomastia results from an imbalance, at the breast tissue level, of the hormones estrogen and androgen. Multiple underlying pathophysiological mechanisms may account for this estrogen-androgen imbalance. These pathophysiological mechanisms can be broadly categorized as having physiologic, pathologic or pharmacologic origins. In most affected individuals, gynecomastia results from the combined effects of multiple pathophysiological mechanisms.

Physiologic gynecomastia may occur in neonatal, pubertal, or senescent individuals. Neonatal onset of the condition is generally transient, and caused by exposure to maternal hormones. Pubertal onset gynecomastia occurs frequently as a result of normal hormonal changes, and usually is self-limiting. In elderly men, gynecomastia occurs based on intrinsic aspects of the aging process, such as progressive primary testicular failure and overall increases in adipose tissue.

Gynecomastia also may result from various pathologic mechanisms that impart an estrogen-androgen imbalance. The imbalance may result from an increase in serum estrogen through such mechanisms as increased hormone production from the testes, adrenal gland or various neoplasms; increased displacement of estrogen relative to androgen from the blood-borne sex hormone binding globulin (SHBG); decreased estrogen metabolism; or the administration of exogenous estrogen or estrogen-like compounds. The estrogen-androgen imbalance also may result from a decrease in androgens or decrease in the effectiveness of androgens from such mechanisms as congenital or acquired gonadal failure, decreased secretion of androgens from the testes, altered metabolism of androgens, increased binding of androgen relative to estrogen by the SHBG or defects in the androgen receptor. Additionally, gynecomastia may be idiopathic, caused by chronic illness or result from an enhanced sensitivity of the breast tissue to normal concentrations of estrogen.

The administration of drugs, acting by a wide variety of mechanisms, also may induce gynecomastia. Both prescription and over-the-counter drugs, as well as recreational drugs, may have this effect. For example, drugs like cimetidine, flutamide and spironolactone block the action of androgen receptors and thereby cause an effective estrogen-androgen imbalance at the breast tissue level. The antifungal ketoconazole is known to inhibit testosterone biosynthesis. Cancer chemotherapeutic agents, including alkylating agents, may produce gynecomastia through a direct testicular effect, and cause increasing serum concentrations of gonadotropins. Further, individuals undergoing highly active antiretroviral therapy (HAART) for HIV/AIDS may also develop gynecomastia.

Environmental and industrial agents, such as pesticides, also can cause gynecomastia.

Due to the variety of underlying mechanisms, no uniformly acceptable method for preventing or treating gynecomastia exists. The main treatment of transient pubescent and drug-induced gynecomastia is sympathetic reassurance of the affected individual (Lazala and Saenger, 2002). Frequently, drug-induced gynecomastia is treated by discontinued administration of the offending agent (Glass, 1994). However, in cases such as treatment of HIV/AIDS with HAART, limited choice of alternative treatments may prevent the discontinuation of the offending agents. Treatment of underlying disorders, such as hepatic dysfunction, hyperthyroidism, hypogonadism or the like, may also improve or resolve gynecomastia. For individuals with prostate cancer who undergo surgical castration or are medically rendered hypogonadal, low-dose radiation therapy has been prospectively used to prevent gynecomastia (Gagnon et al., 1979). In cases like prostate cancer, where the underlying disorder cannot be successfully treated, medical therapy for the improvement of gynecomastia may also be attempted. Finally, where gynecomastia has been long-term or fails to respond to medical therapy, surgical excision of the excessive tissue may occur (Daniels and Taylor, 2001). Ablation of the breast tissue is well known but has significant drawbacks. Surgical complications include donut deformity of the breasts, nipple necrosis, nipple flattening, inversion, or loss of sensation. Besides the obvious expense and risk involved, surgical scars and asymmetry of the nipple-areolar complex often cause more embarrassment to the affected individual than the original condition. In a majority of cases, cosmetically unsatisfactory results occur that may be correctible with pectoral implants or liposuction.

Medical therapy is most effective during the florid phase of gynecomastia, because most treatments focus on decreasing the serum estrogen-androgen ratio which causes the ductal proliferation and its accompanying hyperplasia (Lazala and Saenger, 2002). Testosterone therapy yields generally disappointing results because the hormone is aromatized to estrogen, further exacerbating the estrogen-androgen imbalance. Nonaromatizable testosterone derivatives show some benefit. However, these therapies have many undesirable side effects, such as edema, acne and cramps. Estrogen receptor blockade drugs, such as Tamoxifen, have also been used to treat gynecomastia. Although it is not approved for treatment of gynecomastia in the United States, Gruntmanis and Braunstein (2001) suggest the best treatment results can be expected from the estrogen receptor blockage drug Tamoxifen.

In spite of its benefits, Tamoxifen has significant drawbacks. Its action potentially impacts on every estrogen receptor bearing cell in the body, and as both an agonist and antagonist, tamoxifen provokes a wide range of systemic effects. Tamoxifen is a known genotoxic agent and has been shown to cause hepatocarcinoma in rats. As such, it has been classified by the International Agency for Research on Cancer as a class I human carcinogen. Adverse effects associated with tamoxifen include nausea and vomiting, bone and tumor pain, hypercalcemia, depression, lightheadedness and headaches, alopecia, rash, liver disturbances, cataracts, deep vein thrombosis, pulmonary embolism, and peripheral blood and platelet disorders such as leucopenia, neutropenia, and thrombocytopenia.

Therefore, a strong need still exists for gynecomastia treatments and prophylactics that provoke few systemic side effects.

SUMMARY OF THE INVENTION

The present invention includes a method of treating gynecomastia by administering 4-hydroxy tamoxifen. This treatment approach, preferably implemented topically, effectively resolves the proliferation of breast tissue.

The present invention also includes a method of preventing gynecomastia by administering 4-hydroxy tamoxifen. As with the treatment approach, the prophylactic approach is preferably implemented topically.

For the purposes of prophylaxis and treatment, 4-hydroxy tamoxifen may be administered by any means that delivers it to estrogen receptor-bearing cells in vivo. As noted, it is preferable that the administration be done percutaneously (topically), to avoid the first-pass effect and related liver metabolism of 4-hydroxy tamoxifen. For percutaneous administration, 4-hydroxy tamoxifen may be applied to any skin surface. Application to the breasts during percutaneous administration is advantageous because 4-hydroxy tamoxifen tends to concentrate in local subcutaneous tissues with estrogen receptors.

A broad range of formulations are suitable for performing the invention, but hydroalcoholic solutions and gels are preferred. The concentration of 4-hydroxy tamoxifen in these formulation may vary, but a dose should result in local 4-hydroxy tamoxifen tissue concentrations that effectively oppose estrogenic driven effects.

BRIEF DESCRIPTION OF THE FIGURES

FIG. 1 depicts the metabolism of tamoxifen.
FIG. 2 depicts plasma concentrations of 4-hydroxy tamoxifen in healthy women following cutaneous administration.

DETAILED DESCRIPTION OF THE PREFERRED EMBODIMENTS

An important aspect of the present invention is the surprising discovery that 4-hydroxy tamoxifen, when administered percutaneously, may be effective not only in treating but also in preventing gynecomastia. Moreover, percutaneously administered 4-hydroxy tamoxifen results in lower plasma levels of the drug than the standard dose of oral tamoxifen, which translates to fewer adverse side effects. Accordingly, percutaneous 4-hydroxy tamoxifen is an alternative to tamoxifen for both treatment and prophylaxis in this context.

The compound 4-hydroxy tamoxifen, or 1-[4-(2-N-dimethylaminoethoxy)phenyl]-1-(4-hydroxyphenyl)-2-phenyl-but-1-ene, constitutes an active metabolite of the well characterized anti-estrogen compound, tamoxifen. Due to the presence of a double bond between two carbon atoms, 4-hydroxy tamoxifen exists in two stereoisomeric forms. According to the medical and biochemical literature, isomeric forms of 4-hydroxy tamoxifen are commonly designated as cis and trans isomers. From a purely chemical perspective, however, this designation is not strictly accurate because each double bonded carbon atom does not contain an identical chemical group. Therefore, it is more appropriate to refer to the isomers as E (the so-called cis form) and Z (the so-called trans form) configurations. Both the E and Z isomers of 4-hydroxy tamoxifen, either alone or in combination, are useful according to the present invention. The Z isomer is preferred, however, because it is more active than the E isomer.

4-Hydroxy tamoxifen acts as a selective estrogen receptor modulator (SERM) that exhibits tissue-specificity for estrogen receptive tissues. In breast tissue, it functions as an estrogen antagonist. Studies have shown that 4-hydroxy tamoxifen can regulate the transcriptional activity of estrogen-related receptors, which may contribute to its tissue-specific activity. In vitro, 4-hydroxy tamoxifen exhibits more potency than tamoxifen, as measured by binding affinity to estrogen receptors, or ERs, and a binding affinity similar to estradiol for estrogen receptors (Robertson et al., 1982; Kuiper et al., 1997). Z-4-hydroxy tamoxifen inhibits the growth in culture of normal human epithelial breast cells 100 fold more than Z-tamoxifen (Malet et al., 1988).

Although 4-hydroxy tamoxifen is a tamoxifen metabolite, its usefulness for gynecomastia is not presaged by previous experience with tamoxifen itself. There is a noticeable dearth of published reports testing the efficacy of treatment with 4-hydroxy tamoxifen. In addition, tamoxifen is extensively metabolized in humans, as shown in FIG. 1. Thus, its action in vivo is the net result of individual actions by the parent compound and its metabolite compounds competing for the occupation of receptors within target tissues. For example, see Jordan, 1982. Each of these compounds manifests different and unpredictable biological activities in different cells, determined in part by each compound's individual effect on estrogen receptor conformation. That is, estrogen receptor binding of each compound generates a unique receptor-ligand conformation that recruits different cofactors, and results in varying pharmacologies for the different compounds (Wijayaratne et al., 1999; Giambiagi et al., 1988).

Several examples of these varying effects have been documented. For instance, tamoxifen but not 4-hydroxy tamoxifen is a potent rat liver carcinogen. (Carthew et al., 2001; Sauvez et al., 1999). Additionally, tamoxifen but not 4-hydroxy tamoxifen reportedly initiates apoptosis in p53(−) normal human mammary epithelial cells (Dietze et al., 2001). By contrast, 4-hydroxy tamoxifen exhibits a significant inhibitory effect on estrone sulphatase activity in mammary cancer cell lines, while tamoxifen has little or no effect in this regard (Chetrite et al., 1993).

Methods for preparing 4-hydroxy tamoxifen are well known. For example, U.S. Pat. No. 4,919,937 describes a synthesis, derived from Robertson and Katzenellenbogen, 1982, that occurs in stages:

Stage 1—Reaction between 4-(β-dimethylaminoethoxy)-α-ethyldeoxybenzoin and p-(2-tetrahydropyranyloxy) phenylmagnesium bromide;

Stage 2—Separately from stage 1, formation of 1-(4-hydroxyphenyl)-2-phenyl-1-butanone by hydroxylation of 1,2-diphenyl-1-butanone;

Stage 3—Reaction between the products of stages 1 and 2 to form 1-(4-dimethylaminoethoxyphenyl)-1-[p-2-tetrahydropyranyloxy)phenyl]-2-phenylbutan-1-ol;

Stage 4—Dehydration with methanol/hydrochloric acid produces 1-[p-(β-dimethylaminoethoxy)phenyl]-Z-1-(p-hydroxyphenyl)-2-pheny-1-but-1-ene=4-OH-tamoxifen, a mixture of E and Z isomers;

Stage 5—Separation of the E and Z isomers by chromatography and crystallization to constant specific activity.

According to the present invention, 4-hydroxy tamoxifen may be administered to a patient diagnosed with gynecomastia. The condition preferably will be in its florid phase, as it is believed that 4-hydroxy tamoxifen primarily acts by decreasing the effective estrogen-androgen ratio at the breast tissue level. For example in pubescent males with active and painful gynecomastia, the condition may be treated by topical administration of 4-hydroxy tamoxifen to one or both breasts. Thus, one advantage of topical administration is the option of localized treatment of a single breast if the individual is experiencing only unilateral tissue proliferation.

The present invention also contemplates administration of 4-hydroxy tamoxifen prophylactically, to a patient at increased risk for developing gynecomastia. Many risk factors for gynecomastia are well established. For instance, individuals with prostate cancer who undergo surgical castration or are medically rendered hypogonadal through the use of hormone therapy have an increased incidence of gynecomastia. Prophylactic application of low-dose radiation therapy has been used to prevent gynecomastia from occurring in these patients (Gagnon et al., 1979). A skilled medical practitioner can evaluate the pertinent risk factors to determine whether a patient will benefit from prophylactic use of 4-hydroxy tamoxifen.

Pursuant to the present invention, 4-hydroxy tamoxifen may be administered in any dosage form and via any system that delivers the active compound to breast estrogen receptors in vivo. Preferably, the 4-hydroxy tamoxifen is delivered by "percutaneous administration," a phrase that denotes any mode of delivering a drug from the surface of a patient's skin, through the stratum corneum, epidermis, and dermis layers, and into the microcirculation. This is typically accomplished by diffusion down a concentration gradient. The diffusion may occur via intracellular penetration (through the cells), intercellular penetration (between the cells), transappendageal penetration (through the hair follicles, sweat, and sebaceous glands), or any combination of these.

Percutaneous administration of 4-hydroxy tamoxifen offers several advantages. First, it avoids the hepatic metabolism that occurs subsequent to oral administration (Mauvais-Jarvis et al., 1986). Second, percutaneous administration significantly reduces systemic drug exposure, and the attendant risks from non-specifically activating estrogen receptors throughout the body; this, because topical 4-hydroxy tamoxifen is absorbed primarily into local tissues. In particular, when 4-hydroxy tamoxifen is percutaneously applied to breasts, high concentrations accumulate in the breast tissue, presumably due to many estrogen receptors therein, without creating a high plasma concentration (Mauvais-Jarvis et al., supra). Pursuant to the present invention, therefore, 4-hydroxy tamoxifen may be applied to any skin surface, but preferably to one or both breasts.

Although the invention is not constrained to any particular theory, clinically significant side effects of anti-estrogen agents occur when the agents displace estradiol in non-target tissues. Because 4-hydroxy tamoxifen and estradiol have similar binding affinities for estrogen receptors, a competition between them for receptor binding would be approximately equal when the concentration of each compound approximates that of the other. If the 4-hydroxy tamoxifen concentration exceeds the estradiol concentration, the former will be bound preferentially to the estrogen receptors, and vice versa.

Accordingly, doses of 4-hydroxy tamoxifen that result in plasma concentrations less than about 20 pg/mL, or the mean estradiol concentration in normal men, are preferred. The daily doses to be administered can initially be estimated based upon the absorption coefficients of 4-hydroxy tamoxifen, the breast tissue concentration that is desired, and the plasma concentration that should not be exceeded. Of course, the initial dose may be optimized in each patient, depending on individual responses.

As noted above, by targeting 4-hydroxy tamoxifen to breast tissue, high concentrations can be achieved in that tissue without simultaneously raising 4-hydroxy tamoxifen plasma levels to a point where significant systemic competition for estradiol receptors occurs. As an example, in women, at a percutaneous dose of 1 mg/breast/day, 4-hydroxy tamoxifen concentration in breast tissue exceeds normal estradiol concentrations in breast tissue by a factor of 4. (Barrat et al., 1990; Pujol et al., supra). Moreover, 4-hydroxy tamoxifen applied in this manner reaches concentrations in breast tissue that are an order of magnitude higher than concentrations in plasma, i.e., 10:1. By contrast, the breast tissue to plasma ratio of 4-hydroxy tamoxifen following oral administration of tamoxifen is about 5:1.

In men, breast tissue contains large numbers of ER-positive cells, regardless of age. In fact, men have a higher percentage of ER-positive breast cells than age-matched women without breast disease. Breast tissue from gynecomastia also has a high level of ER expression (Sasano et al., 1996), and a significantly higher level of Ki67 expression, a marker of proliferation (Shoker et al., 2000). Accordingly, male breast tissue, like female breast tissue, can capture 4-hydroxy tamoxifen that has been released through skin.

In a percutaneous formulation, doses on the order of 0.25-2.0 mg/breast/day of 4-hydroxy tamoxifen should achieve the desired result, with doses of about 0.5-1.0 mg/breast/day being preferred. In particular embodiments, the dosage is about 0.25, 0.5, 0.75, 1.0, 1.25, 1.5, 1.75 or 2.0 mg/breast/day of 4-hydroxy tamoxifen.

Percutaneous administration can be accomplished mainly in two different ways: (i) by mixing a therapeutically active compound or its non-toxic pharmaceutically acceptable salt with suitable pharmaceutical carriers and, optionally, penetration enhancers to form ointments, emulsions, lotions, solutions, creams, gels or the like, where an amount of said preparation is applied onto a certain area of the skin, or (ii) by incorporating the therapeutically active substance into patches or transdermal delivery systems according to known technology.

The effectiveness of percutaneous drug administration depends on many factors, including drug concentration, surface area of application, time and duration of application, skin hydration, physicochemical properties of the drug, and partitioning of the drug between the formulation and the skin. Drug formulations intended for percutaneous use take advantage of these factors to achieve optimal delivery. Such formulations often comprise penetration enhancers that improve percutaneous absorption by reducing the resistance of the stratum corneum by reversibly altering its physiochemical properties, changing hydration in the stratum corneum, acting as co-solvent, or changing the organization of lipids and proteins in the intercellular spaces. Such enhancers of percutaneous absorption include surfactants, DMSO, alcohol, acetone, propyleneglycol, polyethylene glycol, fatty acids or fatty alcohols and their derivatives, hydroxyacids, pyrrolidones, urea, essential oils, and mixtures thereof. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics.

The many factors and methods relating to percutaneous drug delivery are reviewed in REMINGTON: THE SCIENCE AND PRACTICE OF PHARMACY, Alfonso R. Gennaro (Lippincott Williams & Wilkins, 2000), at pages 836-58, and in PERCUTANEOUS ABSORPTION: DRUGS COSMETICS MECHANISMS METHODOLOGY, Bronaugh and Maibach (Marcel Dekker, 1999). As these publications evidence, those in the pharmaceutical field can manipulate the various factors and methods to achieve efficacious percutaneous delivery.

4-Hydroxy tamoxifen is a large and very lipophilic molecule; hence, without assistance from penetration enhancers it poorly penetrates the skin. Accordingly, formulations of 4-hydroxy tamoxifen used in the present invention preferably comprise one or more penetration enhancers. Alcohols are preferred enhancers because 4-hydroxy tamoxifen is soluble in alcohol. Isopropyl myristate also is a preferred enhancer.

For percutaneous administration, 4-hydroxy tamoxifen may be delivered in an ointment, cream, gel, emulsion (lotion), powder, oil or similar formulation. To this end, the formulation may comprise customary excipient additives, including vegetable oils such as almond oil, olive oil, peach kernel oil, groundnut oil, castor oil and the like, animal oils, DMSO, fat and fat-like substances, lanolin lipoids, phosphatides, hydrocarbons such as paraffins, petroleum jelly, waxes, detergent emulsifying agents, lecithin, alcohols, carotin, polyols or polyglycols such as glycerol (or glycerine), glycerol ethers, glycols, glycol ethers, polyethylene glycol, polypropylene glycol, non-volatile fatty alcohols, acids, esters, volatile alcoholic compounds, urea, talc, cellulose derivatives, coloring agents, antioxidants and preservatives.

According to the present invention, 4-hydroxy tamoxifen also may be delivered via a transdermal patch. In one embodiment, the patch comprises a reservoir for the 4-hydroxy tamoxifen formula. The patch may comprise (a) a solution-impermeable backing foil, (b) a layer-like element having a cavity, (c) a microporous or semi-permeable membrane, (d) a self-adhesive layer, and (e) optionally, a removable backing film. The layer-like element having a cavity may be formed by the backing foil and the membrane. Alternatively, the patch may comprise (a) a solution-impermeable backing foil, (b) an open-pored foam, a closed-pore foam, a tissue-like layer or a fibrous web-like layer as reservoir, (c) if the layer according to (b) is not self-adhesive, a self-adhesive layer, and (d) optionally a removable backing film.

In preferred embodiments of the invention, 4-hydroxy tamoxifen is formulated in a hydroalcoholic gel. The amount of 4-hydroxy tamoxifen in such a gel may range from about 0.001 to about 2.0 grams of 4-hydroxy tamoxifen per 100 grams of gel. The amount of 4-hydroxy tamoxifen also may range from about 0.01 to about 2.0, about 0.01 to about 1.75, about 0.01 to about 1.5, about 0.01 to about 1.25, about 0.01 to about 1, about 0.01 to about 0.75, about 0.02 to about 0.5, about 0.03 to about 0.4, about 0.04 to about 0.3, about 0.05 to about 0.25, about 0.05 to about 0.2, about 0.05 to about 0.15, or about 0.05 to about 0.1 gram of 4-hydroxy tamoxifen per 100 grams of gel. Preferably, it ranges from about 0.01 to about 0.1 gram of 4-hydroxy tamoxifen per 100 grams of gel. Thus, the amount of 4-hydroxy tamoxifen per 100 grams of gel may be about 0.01, 0.02, 0.03, 0.04, 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.4, 0.45, 0.5, 0.55, 0.6, 0.65, 0.7, 0.75, 0.8, 0.85, 0.9, 0.95, 1.0, 1.1, 1.2, 1.3, 1.4, 1.5, 1.6, 1.7, 1.8, 1.9 or 2.0 grams.

It is also preferred that 4-hydroxy tamoxifen formulations comprise one or more fatty acid esters as a penetration enhancer. One highly preferred example of a fatty acid ester penetration enhancer is isopropyl myristate. When isopropyl myristate is used in a gel, the amount may range from about 0.1 to about 5.0 grams per 100 grams of gel. The amount of isopropyl myristate also may range from about 0.1 to about 4.5, about 0.2 to about 4.0, about 0.3 to about 3.5, about 0.4 to about 3, about 0.4 to about 2.5, about 0.5 to about 2.0, about 0.5 to about 1.9, about 0.5 to about 1.8, about 0.5 to about 1.7, about 0.5 to about 1.6, about 0.5 to about 1.5, about 0.6 to about 1.4, about 0.7 to about 1.3, about 0.8 to about 1.2, about 0.9 to about 1.1, or about 1.0 gram per 100 grams of gel. Preferably, the amount of isopropy myristate ranges from about 0.5 to about 2.0 grams per 100 grams of gel, and most preferably it ranges from about 0.9 to about 1.1 grams per 100 grams of gel.

4-Hydroxy tamoxifen formulations of the invention generally will comprise one or more nonaqueous vehicles. These vehicles should be capable of dissolving both 4-hydroxy tamoxifen and any penetration enhancer used. They also should have a low boiling point, preferably less than 100° C. at atmospheric pressure, to permit rapid evaporation upon contact with the skin. Examples of suitable non-aqueous vehicles include ethanol, isopropanol and ethyl acetate. Ethanol and isopropanol are preferred. In particular, ethanol effectively contributes to the percutaneous absorption of 4-hydroxy tamoxifen by rapidly evaporating upon contact with skin. The amount of nonaqueous vehicle in a gel formulation can range between 40% and 85%, and generally ranges between 54% and 85% by weight. Preferably the amount of nonaqueous vehicle in a gel formulation ranges between 60% and 80%, and more preferably between 65% and 75% by weight.

Formulations also may comprise an aqueous vehicle, which permits solubilization of any hydrophilic molecules in a formulation, and also promotes diffusion of lipophilic molecules from the formulation to the skin. An aqueous vehicle also can regulate pH. Aqueous vehicles include alkalinizing and basic buffer solutions, including phosphate buffered solutions (e.g., dibasic or monobasic sodium phosphate), citrate buffered solutions (e.g., sodium citrate or potassium citrate) and simply purified water. The amount of an aqueous vehicle preferably ranges between 15% and 45% by weight of a gel formulation, and more preferably between 25% and 35%.

Additionally, 4-hydroxy tamoxifen formulations may comprise one or more gelling agents to increase the viscosity of a formulation and/or to function as a solubilizing agent. Depending on the gelling agent's nature, it may constitute between 0.1% and 20% by weight of a formulation, preferably between 0.5% and 10%, more preferably between 0.5% and 5% and still more preferably between 1% and 5%. Preferred gelling agents include carbomers, cellulose derivatives, poloxamers and poloxamines. More particularly, preferred gelling agents are chitosan, dextran, pectins, natural gum and cellulose derivatives such as ethyl cellulose, hydroxypropyl cellulose, hydroxyethyl cellulose, hydroxypropyl methyl cellulose (HPMC), carboxymethyl cellulose (CMC), and the like. One highly preferred gelling agent is hydroxypropyl cellulose.

When a formulation comprises a gelling agent, in particular a non-preneutralized acrylic polymer, it may advantageously also comprise a neutralizing agent. The neutralizing agent/gelling agent ratio preferably is between 10:1 and 0.1:1, more preferably between 7:1 and 0.5:1, and still more preferably between 4:1 and 1:1. A neutralizing agent should form, in the presence of the polymer, salts that are soluble in the vehicle. A neutralizing agent also should permit optimum swelling of polymer chains during neutralization of charges and formation of polymer salts. Useful neutralizing agents include sodium hydroxide, ammonium hydroxide, potassium hydroxide, arginine, aminomethylpropanol, trolamine and tromethamine. Those skilled in the art will select a neutralizing agent according to the type of gelling agent employed in a formulation. When cellulose derivatives are used as gelling agents, however, no neutralizing agents are required.

Table 1 describes the composition of two highly preferred 4-hydroxy tamoxifen gel formulations.

TABLE 1

Composition of 4-Hydroxy Tamoxifen Gel Formulations

|  | Quantity per 100 g of gel | |
| --- | --- | --- |
| Ingredient | 20 mg 4-OHT Gel | 57 mg 4-OHT Gel |
| 4-Hydroxy Tamoxifen | 0.02 g | 0.057 g |
| 95% Ethyl Alcohol, EP-USP | 72 g | 72 g |
| Isopropyl myristate, EP-USP | 1 g | 1 g |
| Hydroxypropylcellulose, EP-USP | 1.5 g | 1.5 g |
| Phosphate Buffer (pH 7, diluted 1:4) | q.s. 100 g | q.s. 100 g |

EP: European Pharmacopoeia;
USP: U.S. Pharmacopoeia

Reference to the following, illustrative examples will help to provide a more complete understanding of the invention.

EXAMPLE 1

Demonstration of Percutaneous 4-Hydroxy Tamoxifen Delivery

Four patients with breast cancer received [$^3$H]-4-hydroxy tamoxifen in an alcoholic solution applied directly to the breasts at specified intervals between 12 hours to 7 days prior to surgery to excise diseased tissue. After surgery, both the excised tissue and the normal breast tissue surrounding the tumor contained radioactivity (Kuttenn et al., 1985).

In a follow-up study, 9 of 12 patients scheduled for surgical excision of hormone-dependent breast cancer received Z-[$^3$H]-4-hydroxy tamoxifen (80 µCi) in a 60% alcoholic solution, and 3 patients received Z[$^3$H]-tamoxifen (80 µCi) for comparison. The patients received [$^3$H]-labeled drug applied directly on the affected breasts at specified intervals ranging from 12 hours to 7 days before surgery to excise diseased tissue. Breast tissue from three regions: the tumor, tissue immediately surrounding the tumor, and normal tissue, was excised and immediately frozen in liquid nitrogen. Additionally, plasma and urine samples were obtained at scheduled intervals and frozen until analysis.

Table 2 shows results from the analyses performed. 4-Hydroxy tamoxifen concentrated predominantly in the cytosolic and nuclear fractions of breast tissue, where estrogen receptors are present. In these intracellular sites, 4-hydroxy tamoxifen remained unmetabolized except for limited isomerization from the Z to the E form. Retention in the breast lasted approximately 4 days in the 4-hydroxy tamoxifen group, but was shorter and far weaker in the tamoxifen group.

TABLE 2

[$^3$H]-4-Hydroxy Tamoxifen and Metabolites Identified in Breast Tumor Tissue Following Percutaneous Administration of Z-[$^3$H]-4-Hydroxy Tamoxifen to the Affected Breast

| | % Metabolites in Breast Tissue | | | | |
| --- | --- | --- | --- | --- | --- |
| Metabolites | 12 hr[1] | 24 hr | 36 hr | Day 4 | Day 7 |
| 4-Hydroxy Tamoxifen | 97 | 94 | 78 | 70 | 65 |
| N-Desmethyl-4-Hydroxy Tamoxifen | 2 | 4 | 14 | 20 | 16 |
| Bisphenol | 1 | 2 | 3 | 8 | 8 |
| N-Desmethyl tamoxifen | | | <1 | <1 | 3-4 |
| Tamoxifen | | | | <1 | 2 |

[1]Time after administration of Z-[$^3$H]-4-hydroxy tamoxifen

The percentage of radioactivity identified as [$^3$H]-4-hydroxy tamoxifen in breast tissue after percutaneous administration decreased slowly over seven days (from 97% to 65%). During this period a progressive isomerization of the Z isomer into the E isomer occurred, with similar percentages observed at day 7 (32% and 33%).

The radioactivity in blood due to [$^3$H]-4-hydroxy tamoxifen increased gradually, with a plateau from days 4 to 6. This contrasts with [$^3$H]-tamoxifen, which rapidly appeared in the blood, plateauing at 2 days. At 36 hours following percutaneous [$^3$H]-4-hydroxy tamoxifen administration, only 0.5% of the radioactivity administered showed in the blood.

In contrast to the near absence of 4-hydroxy tamoxifen metabolism in the breast tissue, marked metabolism occurred in blood. In blood, at 24 hours after administration, 68% of radioactivity represented 4-hydroxy tamoxifen, 18% represented N-desmethyl-4-hydroxy tamoxifen, and 11% represented bisphenol.

Peak urinary elimination occurred at a later time following percutaneous administration of 4-hydroxy tamoxifen compared to percutaneous tamoxifen. Following application of 4-hydroxy tamoxifen, a progressive increase of metabolites, mostly N-desmethyl-4-hydroxy tamoxifen and bisphenol, was observed in the urine.

This example demonstrates that percutaneous application of 4-hydroxy tamoxifen to the breasts results in a substantial and lasting local tissue concentration of the drug, with minimal metabolism, stable and very low plasma concentrations, and slow elimination via the urine. These attributes of percutaneously applied 4-hydroxy tamoxifen are anticipated to be particularly important for the prevention and treatment of gynecomastia.

EXAMPLE 2

Demonstration of the Pharmacokinetics and Pharmacodynamics of Percutaneously Administered 4-OH-Tamoxifen Compared to 20 mg of Oral Tamoxifen This study compared the tissue and plasma concentrations of 4-hydroxy tamoxifen after percutaneous administration via a hydroalcoholic gel with tissue and plasma concentrations of 4-hydroxy tamoxifen after oral administration of tamoxifen (Pujol, 1995).

Thirty-one patients scheduled for breast cancer surgery were randomly assigned to 1 of 5 groups. They received treatment with either oral tamoxifen or percutaneous 4-hydroxy tamoxifen as outlined in Table 3. Treatment was daily and lasted for 3-4 weeks prior to surgery. The study evaluated three different doses of 4-hydroxy tamoxifen (0.5, 1, or 2 mg/day) and two areas of application (either to both breasts or to a large surface of skin including arms, forearms, and shoulders). One group of patients received 20 mg/day (10 mg b.i.d.) of oral tamoxifen (Nolvaldex®).

TABLE 3

Treatment Groups

| | | | | Dose | |
|---|---|---|---|---|---|
| Group | N | Drug | Application Site | mg/breast/day | Total Daily Dose (mg/day) |
| 1 | 6 | PO tamoxifen | — | — | 20[a] |
| 2 | 6 | 4-OHT gel | both breasts | 0.25 | 0.5 |
| 3 | 5 | 4-OHT gel | both breasts | 0.50 | 1 |
| 4 | 5 | 4-OHT gel | arms, forearms, and shoulders | — | 1 |

TABLE 3-continued

Treatment Groups

| | | | | Dose | |
|---|---|---|---|---|---|
| Group | N | Drug | Application Site | mg/breast/day | Total Daily Dose (mg/day) |
| 5 | 6 | 4-OHT gel | arms, forearms, and shoulders | — | 2[b] |

[a]10 mg b.i.d.
[b]divided into 2 daily applications; 1 mg in the morning and 1 mg in the evening The 4-hydroxy tamoxifen gel (20 mg of 4-hydroxy tamoxifen/100 g of hydroalcholic gel; Besins-International Laboratories) was packaged in a pressurized dose-metering pump that delivered 1.25 g of gel/metered dose (i.e., 0.25 mg of 4-hydroxy tamoxifen/dose).

During surgery, two samples (1 cm$^3$ each) of breast tissue were excised, one tumoral and the other macroscopically normal. They were immediately frozen in liquid nitrogen until assayed. Blood samples were obtained on the day of and the day prior to surgery. All tissue and plasma samples were analyzed for 4-hydroxy tamoxifen concentration by gas chromatograph/mass spectrometry (GC-MS).

Pre and post-treatment blood samples were assayed for complete blood counts (CBC), bilirubin, serum glutamic-pyruvic transaminase (SGPT), serum glutamic-oxaloacetic transaminase (SGOT), alkaline phosphatase, creatinine, estradiol, follicle-stimulating hormone (FSH), lutenizing hormone (LH), sex hormone-binding globulin (SHBG), cholesterol, high-density lipoprotein (HDL), low-density lipoprotein (LDL), triglycerides, fibrinogen, and anti-thrombin III.

Table 4 below summarizes the concentration of 4-hydroxy tamoxifen found in breast tissue and plasma. Normal and tumor breast tissues contained similar concentrations of 4-hydroxy tamoxifen in all five treatment groups. 4-hydroxy tamoxifen concentrated at higher amounts in breast tissue when the gel was applied directly to the breasts, rather than to other large skin surfaces.

TABLE 4

Concentrations of 4-hydroxy tamoxifen

Mean ± SD 4-hydroxy tamoxifen (Range)

| | | Plasma Concentrations (pg/mL) | | Normal Tissue | |
|---|---|---|---|---|---|
| Group | N | Day Pre-Surgery | Day of Surgery | (pg/g) | Tumor (pg/g) |
| 1 | 6 | 2326 ± 585 (1371-2959)[a] | 2317 ± 1098 (881-4176) | 10215 ± 2151 (5873-11511) | 12453 ± 3751 (9568-18904)[a] |
| 2 | 6 | 0 (0-0)[a] | 17 ± 27 (0[c]-61) | 353 ± 513 (0[d]-1317) | 1447 ± 2673 (0[f]-6889) |
| 3 | 5 | 164 ± 131 (29-279)[b] | 62 ± 71 (28-190) | 1112 ± 1125 (197-2979) | 1877 ± 2472 (345-6211) |
| 4 | 5 | 94 ± 76 (35-201)[b] | 13 ± 29 (0[e]-65) | 140 ± 130 (0[e]-270) | 552 ± 357 (271-1150) |
| 5 | 6 | 78 ± 138 (0[e]-284)[b] | 73 ± 114 (0[c]-244) | 992 ± 2195 (0[d]-5462) | 224 ± 312 (0[d]-799) |

[a]n = 5
[b]n = 4
[c]4 patients had undetectable levels of 4-hydroxy tamoxifen (LOQ = 20 pg/ml)
[d]3 patients had undetectable levels of 4-hydroxy tamoxifen
[e]2 patients had undetectable levels of 4-hydroxy tamoxifen
[f]1 patient had undetectable levels of 4-hydroxy tamoxifen Side effects did not pose a significant problem. Cutaneous treatment did not cause any local irritation. One woman in Group 2 (0.5 mg/day of 4-hydroxy tamoxifen gel) reported dizzy spells, cystitis, and mild vaginitis occurring on the seventh day of treatment. One woman in Group 1 (oral tamoxifen) reported hot flashes and mild vaginitis on the fifth day of treatment.

No differences existed between the pre- and post treatment blood samples for any of the hematology or serum chemistry evaluations in the patients who received 4-hydroxy tamoxifen gel. However, a statistically significant decrease in anti-thrombin III and fibrinogen and a statistically significant increase in platelet and lymphocyte counts were observed in the oral tamoxifen group, consistent with the biologic effects of this drug observed in other studies. Thus, percutaneously applied 4-hydroxy tamoxifen is an especially attractive method of preventing and treating gynecomastia due to its reduced adverse effects.

EXAMPLE 3

Demonstration of Tolerance and Pharmacokinetics of Percutaneously Administered 4-OH-Tamoxifen in Healthy Women This study demonstrates the tolerance and pharmacokinetics of topically applied 4-hydroxy tamoxifen gel in healthy premenopausal women, aged 18-45. Each participant applied the gel daily for the duration of two menstrual cycles.

Three doses and two gel concentrations were tested, as summarized in Table 5. For Groups A-C, the gel, containing 20 mg of 4-hydroxy tamoxifen/100 g, was dispensed from a pressurized dose-metering pump that delivered 0.25 mg of 4-hydroxy tamoxifen/dose. The study of Group C was suspended because the quantity of gel was too large to be applied to a single breast. Groups D and E received a more concentrated gel that contained almost 3 times as much 4-hydroxy tamoxifen: 57 mg of 4-hydroxy tamoxifen/100 g, or 50 mg of 4-hydroxy tamoxifen/100 mL of gel. This more concentrated gel also was delivered by a dose-metering pump that supplied 0.25 mg of 4-hydroxy tamoxifen/dose.

TABLE 5

Treatment Groups

| Group | N | Dose (mg/day) | Gel Concentration (mg of 4-OHT/g of gel) | Treatment |
|---|---|---|---|---|
| A | 12 | 0.5 | 20 mg/100 g | 1 metered dose/breast/day |
| B | 8 | 1 | 20 mg/100 g | 2 metered doses/breast/day |
| C | 2 | 2 | 20 mg/100 g | study was interrupted |
| D | 12 | 1 | 57 mg/100 g | 2 metered doses/breast/day |
| E | 12 | 2 | 57 mg/100 g | 4 metered doses/breast/day |

At the end of a menstrual cycle, each patient received a single dose, after which serial blood samples were collected at 0, 0.5, 1, 1.5, 2, 3, 4, 6, 12, 18, 24, 36, 48, and 72 hours.

On the first day of the following menstruation, treatment, which consisted of daily application of the gel over two menstrual cycles, began. Blood samples were collected 24 hours following the morning application of gel on days 7, 20 and 25 of the first and second cycles. On the last day of administration, day 25 of the second menstrual cycle, serial blood samples were collected prior to application and at 0.5, 1, 1.5, 2, 3, 4, 6, 12, 18, 24, 36, 48, and 72 hours after application of the gel. The samples were analyzed for 4-hydroxy tamoxifen, estradiol, progesterone, FSH and LH.

Plasma concentrations of 4-hydroxy tamoxifen remained detectable 72 hours after the last gel application. Therefore, to ensure that data points were obtained until 4-hydroxy tamoxifen became undetectable in the blood, additional blood samples were collected from some participants at intervals up to 92 days following the last application of gel.

Table 6 displays the mean±standard deviation (SD) plasma concentrations of 4-hydroxy tamoxifen, with ranges in parentheses. A single 0.5 mg dose did not produce detectable plasma concentrations of 4-hydroxy tamoxifen, but 6 of 12 patients had detectable plasma concentrations (>5 pg/mL) after a single dose of 1 mg.

TABLE 6

Mean ± SD Plasma Concentrations of 4-hydroxy tamoxifen in Healthy Women Following Daily Cutaneous Administration for Two Menstrual Cycles

| Cycle | Day | Time after Application (hr) | 0.5 mg/day (n = 12)[1] | 1 mg/day (n = 8)[1] | 1 mg/day (n = 12)[2] | 2 mg/day (n = 12)[2] |
|---|---|---|---|---|---|---|
| First | 1 | 0 | (0-17.2) | (0-13.9) | (0-9.5) | (0-0) |
|  | 7 | 24 | 6.4 ± 5.6 (<LOQ-16.8) | 15.2 ± 9.7 (<LOQ-26.8) | 14.4 ± 13.1 (<LOQ-37.9) | 26.9 ± 18.2 (8.9-71.3) |
|  | 20 | 24 | 13.6 ± 7.9 (<LOQ-25.9) | 17.3 ± 9.5 (<LOQ-29.8) | 18.1 ± 15.8 (<LOQ-44.5) | 44.0 ± 29.2 (10.5-117.5) |
|  | 25 | 24 | 23.9 ± 23.4 (<LOQ-73.1) | 15.5 ± 6.6 (6.4-25.0) | 19.8 ± 16.2 (6.2-57.0) | 45.4 ± 31.0 (17.9-120.1) |
| Second | 7 | 24 | 25.2 ± 16.1 (6.5-61.7) | 17.4 ± 11.2 (5.7-39.6) | 22.2 ± 16.4 (9.0-64.4) | 42.2 ± 24.8 (18.2-98.0) |
|  | 20 | 24 | 15.7 ± 14.0 (<LOQ-52.3) | 14.8 ± 6.5 (5.4-24.8) | 24.4 ± 20.1 (<LOQ-65.4) | 38.9 ± 27.1 (18.7-119.7) |
|  | 25 | 0[3] | 10.8 ± 9.9 (<LOQ-36.4) | 15.7 ± 17.1 (<LOQ-56.4) | 27.2 ± 20.8 (8.0-72.1) | 43.2 ± 27.7 (16.9-120.3) |
|  |  | 0.5 | 10.9 ± 7.4 (<LOQ-26.0) | 13.5 ± 9.1 (<LOQ-27.7) | 25.9 ± 18.7 (8.7-69.2) | 44.5 ± 29.9 (13.6-124.5) |
|  |  | 1 | 10.4 ± 7.8 (<LOQ-26.7) | 10.8 ± 6.6 (<LOQ-23.8) | 28.7 ± 19.5 (8.8-69.2) | 40.5 ± 25.1 (14.2-106.7) |
|  |  | 1.5 | 9.0 ± 8.2 (<LOQ-25.1) | 11.8 ± 8.0 (<LOQ-23.6) | 25.6 ± 17.8 (7.5-67.0) | 36.8 ± 21.1 (15.9-90.0) |
|  |  | 2 | 11.8 ± 9.5 (<LOQ-26.9) | 10.7 ± 6.9 (<LOQ-24.7) | 25.1 ± 18.0 (6.9-67.3) | 36.8 ± 21.6 (13.0-83.7) |
|  |  | 3 | 10.0 ± 7.9 (<LOQ-23.1) | 11.4 ± 7.9 (<LOQ-28.1) | 24.8 ± 20.5 (9.0-69.9) | 36.1 ± 20.6 (11.9-89.4) |
|  |  | 4 | 9.2 ± 8.3 (<LOQ-25.3) | 11.2 ± 7.3 (<LOQ-25.7) | 26.8 ± 23.3 (6.4-78.1) | 38.1 ± 21.2 (16.5-92.0) |
|  |  | 6 | 11.4 ± 8.5 (<LOQ-26.6) | 10.7 ± 6.4 (<LOQ-22.8) | 25.0 ± 18.2 (9.0-65.3) | 41.0 ± 29.1 (14.0-123.8) |

TABLE 6-continued

Mean ± SD Plasma Concentrations of 4-hydroxy tamoxifen in Healthy Women Following Daily Cutaneous Administration for Two Menstrual Cycles

| | | Time after | Mean ± SD (Range is indicated in parenthesis) in pg/mL | | | |
|---|---|---|---|---|---|---|
| Cycle | Day | Application (hr) | 0.5 mg/day (n = 12)[1] | 1 mg/day (n = 8)[1] | 1 mg/day (n = 12)[2] | 2 mg/day (n = 12)[2] |
| | | 12 | 11.0 ± 9.7 (<LOQ-29.1) | 11.8 ± 7.8 (<LOQ-28.1) | 28.3 ± 22.9 (6.4-74.6) | 45.1 ± 30.6 (18.7-126.8) |
| | | 18 | 9.7 ± 8.8 (<LOQ-24.9) | 12.2 ± 8.3 (<LOQ-29.6) | 23.4 ± 17.4 (8.1-57.9) | 39.8 ± 25.5 (16.0-107.3) |
| | 26 | 24 | 12.4 ± 9.4 (<LOQ-34.4) | 18.6 ± 14.2 (<LOQ-40.1) | 26.0 ± 19.6 (8.9-61.9) | 44.0 ± 33.0 (15.8-132.5) |
| | | 36 | 10.9 ± 6.9 (5.0-25.8) | 13.4 ± 7.5 (<LOQ-25.4) | 25.7 ± 18.4 (8.8-61.3) | 42.1 ± 31.5 (15.1-129.3) |
| | 27 | 48 | 12.1 ± 6.5 (4.8-26.6) | 12.5 ± 6.0 (<LOQ-19.6) | 22.0 ± 16.0 (5.6-50.2) | 38.1 ± 25.3 (17.5-110.0) |
| | 28 | 72 | 9.9 ± 7.1 (<LOQ-22.3) | 9.9 ± 5.8 (<LOQ-19.6) | 18.9 ± 12.4 (5.6-37.8) | 33.2 ± 22.2 (17.7-98.0) |
| | | +5 days | — | 5.8 ± 5.2 (<LOQ-12.4) | 11.4 ± 8.2 (<LOQ-25.8) | 20.4 ± 17.3 (9.1-71.6) |
| | | +8 days | <LOQ | (<LOQ-17.4) | (0-14.8) | 10.8 ± 13.4 (<LOQ-52.0) |
| | | +12 days | (maximum 9.09) | (<LOQ-7.0) | (0-<LOQ) | (0-30.4) |
| | | +20 days | 0 | <LOQ | (0-<LOQ) | (0-<LOQ) |

[1]Gel concentration was 20 mg of 4-hydroxy tamoxifen per 100 g of gel.
[2]Gel concentration was 57 mg of 4-hydroxy tamoxifen per 100 g of gel.
[3]Timepoint 0 is 24 hours after the application on Day 24 and prior to the final application on Day 25.
LOQ = limit of quantification (<5 pg/mL)

FIG. 2 shows a plasma concentration-time curve, following the last administration on day 25 of the second menstrual cycle. Table 7 shows mean pharmacokinetic parameters that relate to the last administration, on day 25 of the second menstrual cycle.

TABLE 7

Mean Pharmacokinetic Parameters of 4-hydroxy tamoxifen in Healthy Women Following the Last Administration

| | Mean ± SD (Range is indicated in parenthesis) | | | |
|---|---|---|---|---|
| Parameter | 0.5 mg/day (n = 12)[a] | 1 mg/day (n = 8)[a] | 1 mg/day (n = 12)[b] | 2 mg/day (n = 12)[b] |
| $C_{max}$ (pg/mL) | 17.0 ± 8.5 (7.6-34.4) | 21.0 ± 14.0 (<LOQ-40.1) | 35.1 ± 22.4 (9.9-78.1) | 51.6 ± 31.7 (22.1-132.5') |
| $t_{max}$ (hr) | 40 ± 81 (0.5-288) | 24 ± 18 (0.5-48) | 12.8 ± 14.9 (1-36) | 11.8 ± 12.3 (0.5-36) |
| $t_{1/2}$ (hr) | — | — | (58-118) | (49-101) |
| $AUC_{0-24}$ (pg · hr/mL) | 256.3 ± 205.3 (24.6-651.1) | 300.9 ± 190.8 (0-693.6) | 619 ± 466 (187-1522) | 998 ± 653 (424-2778) |
| $C_{av} = AUC_{0-24}/24$ (pg/mL) | 10.7 ± 8.5 (1.0-27.1) | 12.5 ± 7.9 (0-28.9) | 25.8 ± 19.4 (7.8-63.4) | 41.6 ± 27.2 (17.7-115.8) |
| T(1stC < LOQ) (hr) | — | 274 ± 141 (144-480) | 236 ± 72 (144-384) | 326 ± 97 (192-480) |

[a]Gel concentration was 20 mg of 4-hydroxy tamoxifen per 100 g of gel.
[b]Gel concentration was 57 mg of 4-hydroxy tamoxifen per 100 g of gel.

$AUC_{0-24}$=area under the concentration-time curve for 0-24 hours; $C_{av}$=Calculation of area under the curve over 24 hours ($AUC_{0-24}$) divided by 24 hours; $C_{max}$=maximal concentration in plasma; $t_{1/2}$=half-life; T(1stC<LOQ)=first timepoint at which the plasma concentration was below the limit of quantification; $t_{max}$=time of maximal concentration in plasma.

The data are consistent with a dose response across the three doses tested (0.5, 1, and 2 mg). The more concentrated gel was better absorbed, by approximately double, than the less concentrated gel, based on AUC and $C_{av}$.

Biological tolerance was excellent in all 36 patients. The treatment did not affect FSH, LH, estradiol, or progesterone hormone levels during the menstrual cycles. Moreover, echographic examination of the ovaries at the end of treatment was normal in all patients, showing normal sized developing follicles. One patient developed an allergic reaction to the gel, and 10 reported facial acne (5 of which had a past history of acne).

In summary, this study indicates that the exposure to 4-hydroxy tamoxifen after topical application increases with dose, that plasma concentrations of 4-hydroxy tamoxifen are lower than typical estradiol concentrations (80 pg/mL), and that there is no detectable laboratory or clinical evidence of systemic effects. Because of this, it is anticipated that the percutaneous application of 4-hydroxy tamoxifen will be especially useful in for the prevention and treatment of gynecomastia.

CITED PUBLICATIONS

Each of the following references, in its entirety, is incorporated herein by reference:

Barrat, J., B. de LigniIIres, L. Marpeau, L. Larue, S. Fournier, K. Nahoul, G. Linares, H. Giorgi, and G. Contesso, Effet in vivo de l'administration locale de progestIIrone sur l'activitII mitotique des galactophores humains, J. Gynecol. Obstet. Biol. Reprod. 19: 269-274 (1990) (French).

Braunstein, G. D., Aromatase and gynecomastia, Endocr. Relat. Cancer, 6: 315-24 (1999).

Bronaugh and Maibach, Percutaneous Absorption: Drugs Cosmetics Mechanisms Methodology, Marcel Dekker 1999.

Carthew, P., P. N. Lee, R. E Edwards, R. T. Heydon, B. M. Nolan, E. A. Martin, Cumulative exposure to tamoxifen: DNA adducts and liver cancer in the rat, Arch. Toxicol., 75: 375-80 (2001).

Chetrite, G., C. Varin, L. Delalonde, J. R. Pasqualini, Effect of promegestone, tamoxifen, 4-hydroxytamoxifen and ICT 164,384 on the oestrone sulphatase activity of human breast cancer cells, Anticancer Res., 13(4) 931-4 (July-August 1993).

Daniels, I. R. and G. T. Taylor, Gynecomastia, Eur. J. Surg., 167: 885-92 (2001).

Dietze, E. C., L. E. Caldwell, S. L. Grupin, M. Mancini, and V. L. Seewald, Tamoxifen, but not 4-hydroxytamoxifen initiates apoptosis in p53(−) normal human mammary epithelial cells by inducing mitochondrial depolarization, J. Biol. Chem., 276(7): 5384-94 (Feb. 16, 2001).

Gagnon, J. D. W. T. Moss, K. R. Stevens, Pre-estrogen irradiation for patients with carcinomia of the prostate: a critical review, J. Urol., 121: 182-84 (1979).

Giambiagi, N. and J. R. Pasqualini, Immunological differences between the estradiol-, tamoxifen and 4-hydroxytamoxifen estrogen receptor complexes detected by two monoclonal antibodies, J. Steroid Biochem., 30(1-6): 213-7 (1988).

Glass, A. R., Gynecomastia, Endocrinol. Metab. Clin. North Am.: Clinical Andrology, 23: 825-35 (1994).

Gruntmanis, U. and G. D. Braunstein, Treatment of gynecomastia, Curr. Opin. Investig. Drugs, 2: 643-649 (2001).

Jordan, V. C., Metabolites of tamoxifen in animals and man: identification, pharmacology, and significance, Breast Cancer Res. Treat., 2(2) 123-38 (1982).

Kuiper, G. G. J. M., B. Carlsson, K. Grandien, E. Enmark, J. Heggblad, S. Nilsson, J. Gustafsson, Comparison of the ligand binding specificity and transcript tissue distribution of estrogen receptors α and β, Endocrinology, 138: 863-870 (1997).

Kuttenn, F. and P. Mauvais-Jarvis, Intratumoral levels and metabolism of 4-hydroxytamoxifen after percutaneous administration at the breast level, C. R. Acad. Sci. III. 300: 457-462 (1985) (French).

Lazala, C. and P. Saenger, Pubertal Gynecomastia, J. Pediatr. Endocrinol. Metab. 15: 553-560 (2002).

Malet C., A. Gompel, P. Spritzer, N Bricourt, N H Yaneva, I. Mowszowicz, F. Kutten and P Mauvais Jarvis, Tamoxifen and hydroxytamoxifen isomers versus estradiol effects on normal human breast cells in culture, Cancer Research, 48: 7193-7199 (1988).

Mathur, R. and G. D. Braunstein, Gynecomastia: pathomechanisms and treatment strategies, Horm. Res., 48: 95-102 (1997).

Mauvais-Jarvis, P., N. Baudot, D. Castaigne, P. Banzet, and F. Kuttenn, Trans-4-hydroxytamoxifen concentration and metabolism after local percutaneous administration to human breast, Cancer Research, 46: 1521-1525 (1986).

Pujol, H., J. Girault, P. Rouanet, S. Fournier, J. Grenier, J. Simony, J. B. Fourtillan, and J. L. Pujol, Phase 1 study of percutaneous 4-hydroxy-tamoxifen with analyses of 4-hydroxy-tamoxifen concentrations in breast cancer and normal breast tissue, Cancer Chemother. Pharmacol., 36: 493-498 (1995).

Remington: The Science and Practice of Pharmacy, Alfonso R. Gennaro, Lippincott Williams & Wilkins, 2000, pp. 836-858.

Robertson and Katzenellenbogen, J. Org. Chem., 47: 2387 (1982).

Robertson, D. W., J. A. Katzenellenbogen, D. J. Long, E. A. Rorke and B. S. Katzenellenbogen, Tamoxifen antiestrogens. A comparison of the activity, pharmacokinetics, and metabolic activation of the cis and trans isomers of tamoxifen, J. Steroid Biochemistry, 16(1): 1-13 (1982).

Sasano, H., M. Kimura, S. Shizawa, N. Kimura and H. Nagura, Aromatase and steroid receptors in gynecomastia and male breast carcinoma: An immunohistochemical study, J. Clin. Endocrinol. Metab., 81: 3063-3067 (1996).

Sauvez, F., D. Salin-Drouin, M. Attia, H. Bertheux, and R. Forster, Cutaneously applied 4-hydroxytamoxien is not carcinogenic in female rats. Carcinogenesis, 20: 843-50 (1999).

Shoker, B. S., C. Jarvis, R. B. Clarke, E. Anderson, C. Munro, M. P. A. Davies and D. R. Sibson, J. P. Sloane, Abnormal regulation of the oestrogen receptor in benign breast lesions. J. Clin. Pathol., 53: 778-783 (2000)

Wijayaratne, A. L., S. C. Nagel, L. A. Paige, D. J. Christensen, J. D. Norris, D. M. Fowlkes, and D. P. McDonnell, Comparative Analyses of Mechanistic Difference among Antiestrogens, Endocrinology, 140(12): 5828-5840 (1999).

What is claimed is:

1. A method of treating a male patient suffering from gynecomastia, comprising percutaneously administering an effective amount of 4-hydroxy tamoxifen to said patient, wherein said 4-hydroxy tamoxifen is in a vehicle comprising isopropyl myristate.

2. A method according to claim 1, wherein about 0.25 to 2.0 mg/breast of said 4-hydroxy tamoxifen is administered to said patient per day.

3. A method according to claim 1, wherein about 0.5 to 1.0 mg/breast of said 4-hydroxy tamoxifen is administered to said patient per day.

4. A method according to claim 1, wherein about 0.25 mg/breast of said 4-hydroxy tamoxifen is administered to said patient per day.

5. A method according to claim 1, wherein about 0.5 mg/breast of said 4-hydroxy tamoxifen is administered to said patient per day.

6. A method according to claim 1, wherein about 0.75 mg/breast of said 4-hydroxy tamoxifen is administered to said patient per day.

7. A method according to claim 1, wherein about 1.0 mg/breast of said 4-hydroxy tamoxifen is administered to said patient per day.

8. A method according to claim 1, wherein said 4-hydroxy tamoxifen is formulated in a hydroalcoholic gel.

9. A method according to claim 8, wherein said hydroalcoholic gel comprises ethyl alcohol, isopropyl myristate, and hydroxypropylcellulose.

10. A method according to claim 1, wherein said 4-hydroxy tamoxifen is formulated in an alcoholic solution.

11. A method according to claim 8, wherein said hydroalcoholic gel comprises isopropyl myristate, an aqueous vehicle, an alcoholic vehicle and a gelling agent.

12. A method according to claim 11, wherein said hydroalcoholic gel comprises:
   a) about 0.01% to 0.25% by weight of 4-hydroxy tamoxifen,
   b) about 0.5% to 2% by weight of isopropyl myristate,
   c) about 65% to 75% by weight of absolute alcohol,
   d) about 20% to 35% by weight of aqueous vehicle,
   e) about 0.5% to 5% by weight of gelling agent,
   wherein the percentage of components are weight to weight of the hydroalcoholic gel.

13. A method according to claim 12, wherein said 4-hydroxy tamoxifen constitutes about 0.01%, 0.02%, 0.03%, 0.04%, 0.05%, 0.06%, 0.07%, 0.08%, 0.09%, or 0.10% by weight of the hydroalcoholic gel.

14. A method according to claim 12, wherein said 4-hydroxy tamoxifen constitutes about 0.11%, 0.12%, 0.13%, 0.14%, 0.15%, 0.16%, 0.17%, 0.18%, 0.19%, 0.2%, 0.21%, 0.22%, 0.23%, 0.24%, or 0.25% by weight of the hydroalcoholic gel.

15. A method according to claim 12, wherein said isopropyl myristate constitutes about 0.5%, 0.6%, 0.7%, 0.8%, 0.9%, 1.0%, 1.1%, 1.2%, 1.3%, 1.4%, 1.5%, 1.6%, 1.7%, 1.8%, 1.9% or 2.0% by weight of the hydroalcoholic gel.

16. A method according to claim 12, wherein said alcohol is ethanol or isopropanol, and constitutes in absolute form about 62% to 75% by weight of the hydroalcoholic gel.

17. A method according to claim 12, wherein said aqueous vehicle is a phosphate buffered solution, and constitutes about 25% to 35% by weight of the hydroalcoholic gel.

18. A method according to claim 12, wherein said gelling agent is selected from the group consisting of polyacrylic acids, hydroxypropylcellulose, ethyl cellulose, hydroxyethyl cellulose, hydroxypropyl methyl cellulose, and carboxymethyl cellulose, and constitutes about 0.5% to 5% by weight of the hydroalcoholic gel.

19. A method according to claim 12, wherein said hydroalcoholic gel further comprises a neutralizing agent selected from the group consisting of sodium hydroxide, ammonium hydroxide, potassium hydroxide, arginine, aminomethylpropanol, trolamine and tromethamine, which neutralizing agent constitutes about 0.1% to 5% by weight of the hydroalcoholic gel.

20. A method according to claim 12, wherein said hydroalcoholic gel is packaged in a unit dose packet or in a multiple dose container with a metered pump.

* * * * *